United States Patent [19]

Kudo et al.

[11] Patent Number: 5,863,503
[45] Date of Patent: Jan. 26, 1999

[54] NITROGEN OXIDE DETECTING SENSOR AND METHOD OF MANUFACTURING THE SAME

[75] Inventors: Shuzo Kudo, Nara; Hisao Ohnishi, Osaka; Masamichi Ipponmatsu, Nishinomiya; Shoji Tanaka, Tokyo; Hisao Yamauchi, Nagareyama; Satoshi Takano, Ryugasaki; Mitsunobu Wakata, Sagamihara, all of Japan

[73] Assignees: Osaka Gas Co., Ltd., Osaka, Japan; International Superconductivity Technology Center, Tokyo, Japan; Mitsubishi Denki KK, Tokyo, Japan

[21] Appl. No.: 626,007

[22] Filed: Apr. 1, 1996

Related U.S. Application Data

[63] Continuation-in-part of Ser. No. 268,911, Jun. 30, 1994, abandoned.

[30] Foreign Application Priority Data

Jun. 30, 1993 [JP] Japan ..................................... 5-160985

[51] Int. Cl.⁶ .................................................. G01N 27/04
[52] U.S. Cl. ................................ 422/83; 422/90; 422/94; 422/98; 436/116; 436/117; 436/118; 73/31.05; 204/425; 204/429
[58] Field of Search ................................. 422/83, 90, 94, 422/98; 436/116–118, 136–137; 73/23.2, 31.05, 31.06; 204/425–427, 429; 338/34, 36, 38; 427/124–125, 126.3, 584–586

[56] References Cited

U.S. PATENT DOCUMENTS

| | | | |
|---|---|---|---|
| 4,193,965 | 3/1980 | Cullingford et al. | 422/98 X |
| 4,574,264 | 3/1986 | Takahashi et al. | 422/98 X |
| 4,938,928 | 7/1990 | Koda et al. | 422/98 X |
| 4,940,693 | 7/1990 | Shappiro et al. | 505/1 |
| 4,953,387 | 9/1990 | Johnson et al. | 422/98 X |
| 5,210,070 | 5/1993 | Nagaishi et al. | 505/1 |
| 5,278,138 | 1/1994 | Ott et al. | 505/1 |

FOREIGN PATENT DOCUMENTS

| | | |
|---|---|---|
| 336450 | 10/1989 | European Pat. Off. . |
| 5-332972 | 12/1993 | Japan . |
| 2166247 | 4/1986 | United Kingdom . |

OTHER PUBLICATIONS

H.C. Montgomery *J. Appl. Phys.* 1971, 42, 2971–2975.
H. Niu et al. *Japan. J. Appl. Phys.* 1989, 28, L784–L786.
M. Oda et al. *Solid State Commun.* 1990, 74, 1321–1326.
I. Halasz et al. *Catalysis Lett.* 1991, 11, 327–334.
E. Grantscharoua et al. *Chem. Lett.* 1991, 1759–1762.
P. Mandal et al. *Phys. Rev. B* 1991, 43, 13102–13111.
F. Munakata et al. *Physica C* 1992, 190, 471–476.
I. Nowik et al. *Phys. Rev. B* 1992, 45, 4912–4915.
J.B. Mandal et al. *Physica C* 1993, 216, 195–198.
P. Almeras et al. *Solid State Commun.* 1993, 87, 425–427.
X.J. Huang et al. *Solid State Ionics* 1994, 72, 338–343.
M.A. van Veenendaal. et al, *Phys. Rev. B* 1993, 47, 446–450.
X.J. Huang, L.Q. Chen and J. Schoonman, "High $T_c$ Superconductors as $NO_x$ and $CO_x$ Sensor Materials", *Solid State Ionics*, 57 (1992) pp. 7–10.
Noritaka Mizuno, Hisashi Toyama, Mika Tanaka, Mika Yamato and Makoto Misono, "Reaction Between Nitrogen Monoxide and Carbon Monoxide Over Superconducting Bi–Sr–Ca–Cu and Related Mixed Oxides", *The Chemical Society of Japan; Bull. Chem. Soc. Jpn.*, 64, (1991) pp. 1383–1385.
Tsuyoshi Arakawa and Gin–ya Adachi, "The Direct Reaction Between Nitric Oxide and The Superconductor $YBa_2Cu_3O_{7-\delta}$", *Mat. Res. Bull.*, vol. 24, (1989), pp. 529–534.
Kudo et al., "Nitrogen Oxide Detecting Sensor", *Patent Abstracts of Japan*, Mar. 17, 1994; vol. 18, p. 162.

*Primary Examiner*—Arlen Soderquist
*Attorney, Agent, or Firm*—Hazel & Thomas, PC

[57] ABSTRACT

A nitrogen oxide detecting sensor, according to the present invention, incorporates a gas detecting portion including, as a main component thereof, an oxide compound having electric conductivity or semiconductivity, the oxide compound having a crystal structure of 2212 phase and expressed generally as: $Bi_2Sr_2(Ca_{1-x} Y_x)Cu_2 O_{8\pm\delta}$ where $0.6 \leq x < 1$; $0 \leq \delta \leq 1$. Electrodes are electrically connected to the gas detecting portion. When the gas detecting portion is analyzed by X-ray diffraction using $cuK\alpha$ rays to obtain diffraction peak values thereof in the range of a diffraction angle between 5° and 65°, the diffraction peak values having a sum $\Sigma$ I[2212] expressed by one of the following:

(a) $\Sigma$ I[2212]/$\Sigma$ I[T]>88.1%

(b) {$\Sigma$ I[2212]+$\Sigma$ I[2201]}/$\Sigma$ I[T]>94.8%

(c) {$\Sigma$ I[2212]+$\Sigma$ I[$Y_2O_3$]} $\Sigma$ I[T]>88.1%

(d) {$\Sigma$ I[2212]+$\Sigma$ I[(Bi, Ca) O]}/$\Sigma$ I[T] >88.8% where $\Sigma$ I[2201] is a sum of diffraction peak intensity values based on the 2201 phase; $\Sigma$ I[$Y_2O_3$] is a sum of diffraction peak intensity values based on $Y_2O_3$; $\Sigma$ I[(Bi, Ca)O] is a sum of diffraction peak intensity values based on an oxide including one or both of Bi and Ca and excluding any other metal; and $\Sigma$ I[T] is a sum of diffraction peak intensity values of an oxide including at least one of Bi, Sr, Ca, Y and Cu.

19 Claims, 7 Drawing Sheets

NITROGEN OXIDE DETECTING SENSOR AND METHOD OF MANUFACTURING THE SAME

This application is a continuation-in-part filed under 37 C.F.R. § 1.53 of U.S. patent application Ser. No. 08/268,911 filed Jun. 30, 1994, now abandoned, on behalf of the inventors, Shuzo Kudo, Hisao Ohnishi, Masamichi Ipponmatsu, Satoshi Takano, Mitsunobu Wakata, Hisao Yamauchi and Shoji Tanaka.

BACKGROUND OF THE INVENTION

1. Field of the Invention

The present invention relates to a nitrogen oxide detecting sensor and a method of manufacturing the sensor and more particularly to a nitrogen oxygen sensor to be used in the art of reducing or decomposing nitrogen oxide and a method of manufacturing such sensor.

2. Description of the Related Art

As the conventional methods of measuring a concentration of nitrogen oxide in exhaust gas, there are known the chemiluminescence method, infrared absorbing analysis method, ultraviolet ray absorbing analysis method, controlled potential electrolysis method and controlled potential coulomb method.

Further, in recent years, there is a growing scientific interest to employ, as an oxide semiconductor sensor, a compound expressed by:

$$YBa_2Cu_3O_{7-\delta}$$

At present, the chemiluminescence method is considered as the most promising of all for its highest measurement precision and reliability. However, this method requires such components as an ozone generator, a photomultiplier tube, and a high voltage source. Thus, this method suffers from limitations in the degrees of system size reduction, cost reduction and maintenance conditions that are possible.

When high detection precision is not needed, the controlled potential electrolysis method is convenient. This method, however, suffers from the problems of secular or long-term changes in the electrodes and of having to maintain the electrolysis solution.

Moreover, the devices employed by these methods cost hundreds or thousands of dollars. Also, while the measurement precisions are high, the methods require calibration due to the occurrence of drift and the devices employed have the problem of durability.

On the other hand, the above-described oxide semiconductor sensor has the problem that its sensitivity characteristics are subject to change if water is present in the detection environment.

Further, it is also known that an oxide compound having a composition of: Bi:Sr:$(Ca_{1-x} Y_x)$:Cu=2:2:1:2 is subject to changes in its resistance value due to the presence of NO or $NO_2$, and therefore can be used as a gas detecting portion of a sensor. However, even with this sensor having such an oxide compound, if the sensor is exposed to a high concentration of nitrogen dioxide ($NO_2$), the resistance value at the gas detecting portion remains raised, not returning to the lower original value. Hence, in the detecting portion, there occurs drifting in the base resistance value, i.e., the zero reference point, due to aging such that the sensor becomes unable to provide its sensor function. For this reason, in spite of its superior selectivity to $NO_x$, the above-described composite oxide having a composition of: Bi:Sr:$(Ca_{1-x} Y_x)$:Cu=2:2:1:2 has not been put into practice.

Accordingly, a primary object of the present invention is to provide a nitrogen oxide sensor that is simple in its construction, economical and durable. In addition, the primary object is to provide a method of manufacturing such a sensor.

A further object of the invention is to provide a sensor having superior selectivity to $NO_x$ and comprising an oxide compound that has the composition: Bi:Si$(Ca_{1-x}Y_x)$:Cu=2:2:1:2, the compound including a 2212 phase crystalline structure at more than a predetermined ratio, such that when exposed to a high concentration of $NO_x$, the sensor is capable of immediately returning to its original resistance value, i.e., its zero point when exposed later to a gas not containing $NO_x$.

SUMMARY OF THE INVENTION

For accomplishing the above-noted objects, a nitrogen oxide detecting sensor, according to the present invention, comprises:

a gas detecting portion including, as a main component thereof, an oxide compound having electric conductivity or semiconductivity, said oxide compound having a crystal structure of 2212 phase and expressed generally as:

$$Bi_2Sr_2(Ca_{1-x} Y_x)Cu_2 O_{8\pm\delta}$$

$$(0.6 \leq x < 1; \ 0 \leq \delta \leq 1)$$

and electrodes electrically connected to said gas detecting portion.

wherein said "main component" satisfies the following conditions:

When said gas detecting portion is analyzed by X-ray diffraction using CuKα rays to obtain diffraction peak values thereof in the range of a diffraction angle between 5° and 65°, the diffraction peak values having a sum $\Sigma$ I[2212] expressed by one of the following:

(a) $\Sigma$ I[2212]/$\Sigma$ I[T]>88.1%

(b) {$\Sigma$ I[2212]+$\Sigma$ I[2201]}/$\Sigma$ I[T]>94.8%

(c) {$\Sigma$ I[2212]+$\Sigma$ I[$Y_2O_3$]} $\Sigma$ I[T]>88.1%

(d) {$\Sigma$ I[2212]+$\Sigma$ I[(Bi, Ca) O]}/$\Sigma$ I[T]>88.8% where:

$\Sigma$ I[2201] is a sum of diffraction peak intensity values based on the 2201 phase;

$\Sigma$ I[$Y_2O_3$] is a sum of diffraction peak intensity values based on $Y_2O_3$;

$\Sigma$ I[(Bi, Ca) O] is a sum of diffraction peak intensity values based on an oxide including one or both of Bi and Ca and excluding any other metal;

$\Sigma$ I[T] is a sum of diffraction peak intensity values of an oxide including at least one of Bi, Sr, Ca, Y and Cu, for instance, $Bi_2Sr_2 (Ca_{0.2}Y_{0.8}) CU_2O_{8 \pm\delta}$, $Y_2O_3$ (a compound including an element except Bi, Sr, Ca, Y, and Cu; for instance, $SrTiO_3$ is excluded.)

However, the gas detecting portion may include a stable oxide including an element except Bi, Sr, Ca, Y and Cu, e.g., $SrTiO_3$, $SiO_2$ or the like). These compounds do not affect the $NO_x$ detecting function, but just enhance the mechanical or chemical strength of the material forming the gas detecting portion.

According to one aspect of the present invention, a nitrogen oxide detecting sensor comprises:

a gas detecting portion comprised mainly of an oxide compound having electric conductivity or semiconductivity and resistivity ranging not more than 50 Ω cm and expressed generally as:

$$(0.6 \leq x < 1.0; \ 0 \leq \delta \leq 1)$$

and electrodes electrically connected to said gas detecting portion.

Functions and effects of these constructions will be described next.

With the oxide compounds used in the gas detecting portion of these sensors, $NO_x$ reversibly adsorbs thereto and desorbs or is released therefrom, according to the $NO_x$ concentration in the gas phase. With the occurrence of the adsorption reaction, the gas detecting portion experiences a change in its ohmic resistance value according to the concentration of the nitrogen oxide in the gas phase. This resistance change is detected by the electrodes of the sensor, so that the sensor functions as a nitrogen oxide detecting sensor.

Then, even if the oxide compound satisfies the requirement of the above-described general composition formula, if this compound has more than a predetermined amount of crystal structure other than 2212 phase or a resistivity more than 50 Ω cm (as will be described in sample experiments to follow, if the crystal structure includes any other phase than the 2212 phase at more than a predetermined ratio, its resistivity too substantially satisfies this condition), the sensitivity tends to be lower. Accordingly, such a sensor is not useful. Therefore, in order for the sensor to work effectively, this sensor needs to satisfy the above-described conditions.

As described above, with the sensor according to the present invention, through the measurement of a change in the ohmic resistance in the gas detecting portion via the electrodes, it is possible to detect, with a practically sufficient level of sensitivity, the concentration of nitrogen oxide gas alone included within the atmosphere or a combustion exhaust gas. Further, since this sensor comprises such a simple combination of an oxide compound and electrodes, the present invention embodies a sensor that is simple and inexpensive in its construction, and whose method of manufacture is also simple and inexpensive.

In general, in manufacturing the oxide compound having the above-specified composition: $Bi:Sr(Ca_{1-x}Y_x):Cu=2:2:1:2$, other compounds, than the target 2212 phase, are apt to be inadvertently generated also. Thus, it is extremely difficult to manufacture a gas detecting portion comprised of a single phase of 2212 phase. Then, through various analytical methods, it has been found that some types of compounds present in the gas detecting portion other than the 2212 phase react with nitrogen dioxide to generate nitrates which causes irreversible changes in the resistance value of the gas detecting portion. Further, even if the gas detecting portion contains such non-2212 phase compounds in such small amounts as to not cause any adverse effect if the oxide compound having the composition: $Bi:Sr(Ca_{1-x}Y_x):Cu=2:2:1:2$ were used as a superconductive material, this gas detecting portion is useless as a $NO_x$ detecting portion, in terms of response recoverability and durability.

Based on the above findings, further studies have been conducted on the gas detecting portion for the following purposes:

a) to minimize composition variations due to evaporation of a certain element in the course of the heating process employed in the manufacture of the gas detecting portion; and b) to restrict the production of oxides containing Ca and Cu that occurs in the crystalization process of the oxide compound having the composition: $Bi:Sr(Ca_{1-x}Y_x):Cu=2:2:1:2$, wherein 2201 phase is generated at a temperature lower than a temperature where the 2212 phase is generated.

The above studies have provided the following further findings:

Even when a non-2212 phase compound co-exists, if the presence ratio of this compound is limited below a predetermined value, then there occurs no adverse effect on the resistance value of the sensor or the response recoverability thereof after contact with $NO_x$.

In the case of compounds expressed by: $(Ca_{1-l}Sr_l)CuO_2$ $(0 \leq l \leq 1)$, or $(Ca_{5-m}Sr_m)CuO_{5\pm\delta}(0 \leq m \leq 5)$, such compounds react with nitrogen dioxide to become nitrates thereby leading to irreversible changes in the resistance value. On the other hand, in the face of a further compound of 2201 phase, as expressed by $Y_2O_3$, $(Bi_{1-y}Ca_y)O_{2+z}(0 \leq y \leq 1; 0 \leq z \leq 1)$ or the like, the above compounds do not cause any irreversible change.

Therefore, such compounds cause no inconvenience when present in the gas detecting portion.

Based on these findings, the present invention has been developed to address the shortcomings of the prior art.

Further objects, features and effects of the invention will become more apparent from the following more detailed description of the embodiments of the invention with reference to the accompanying drawings.

DESCRIPTION OF THE PREFERRED EMBODIMENTS

Preferred embodiments of a nitrogen oxide sensor relating to the present invention will be described next with reference to the accompanying drawings. The embodiments will be described in the order of construction, manufacturing methods and characteristics of the sensors.

Sensor Construction

Figure 1:
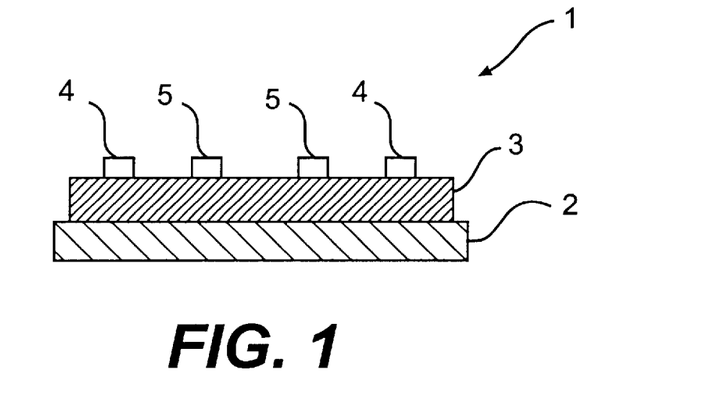
FIG. 1 is a view showing a construction of a sensor according to one preferred embodiment of the present invention.
Figure 2A:
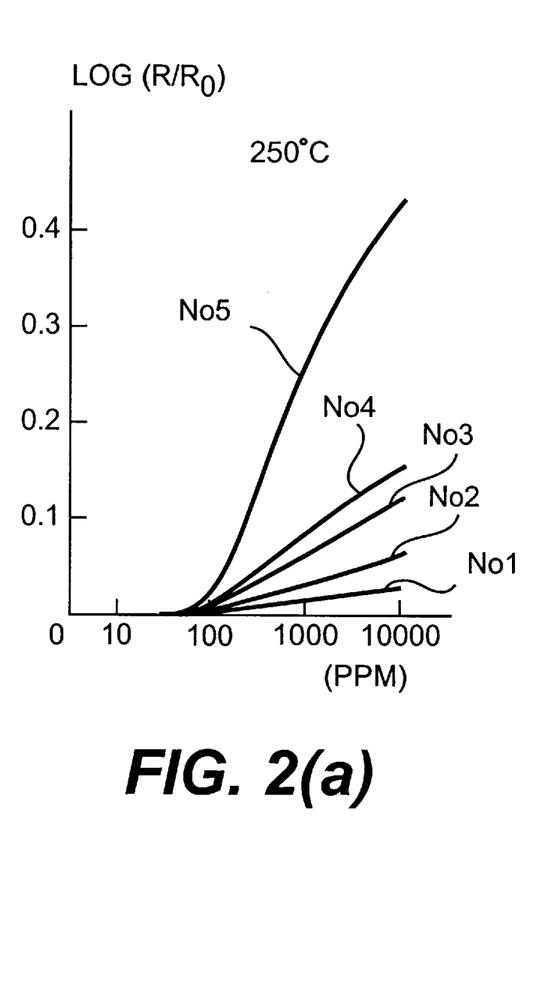
FIGS. 2(a), (b), (c) and (d) show sensitivity characteristics of the sensor to target gas at various temperatures.
Figure 2B:
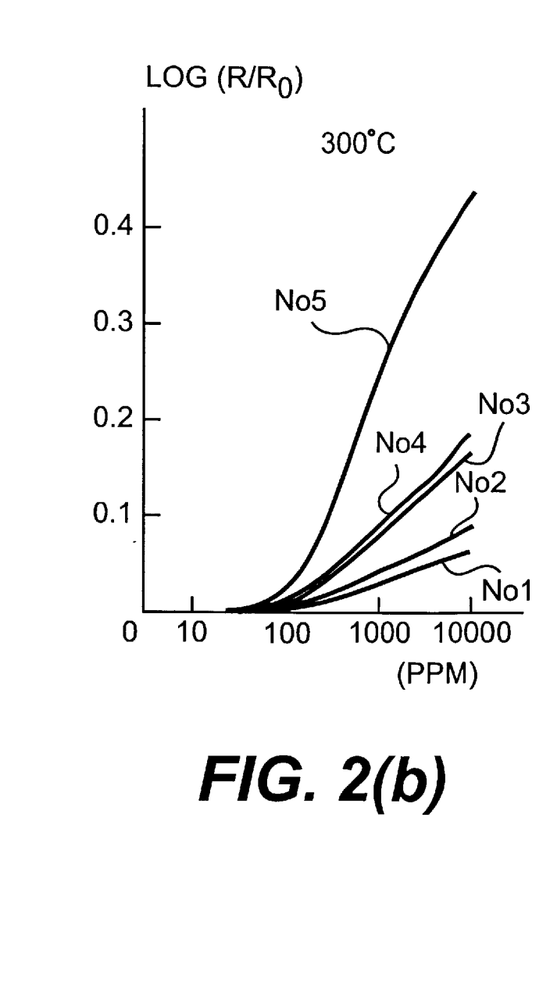
Figure 2C:
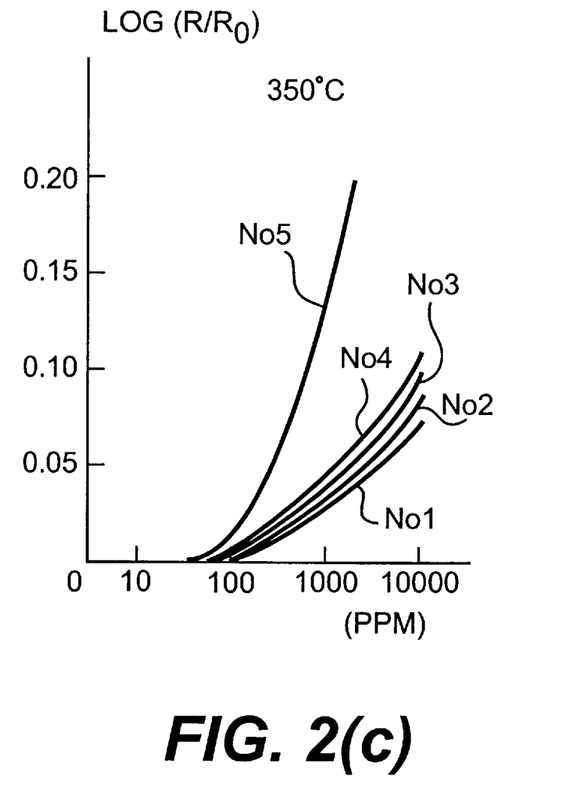
Figure 2D:
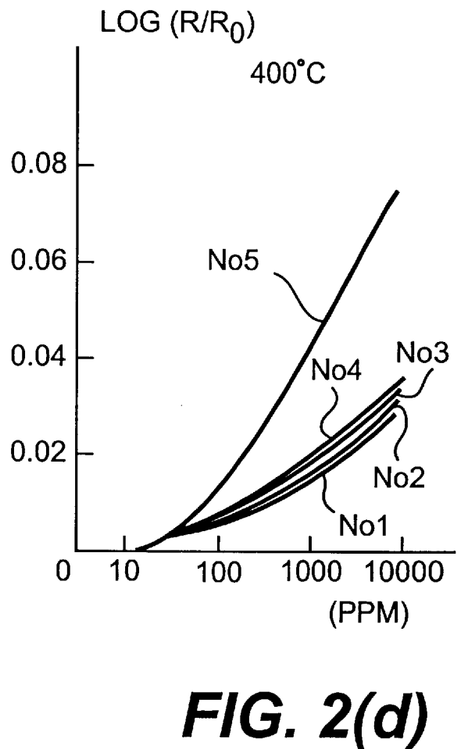

FIG. 1 shows the construction of a nitrogen oxide detecting sensor 1 according to one preferred embodiment. This nitrogen oxide detecting sensor 1 includes a heating base plate 2 comprised of a ceramic heater plate and a lump-shaped gas detecting portion 3 formed on the base plate 2 and comprised of an oxide compound of predetermined composition according to the present invention. For this gas detecting portion 3, there are provided a pair of current applying Pt electrodes 4 and a corresponding pair of potential detecting electrodes 5 for the current applying electrodes 4. In the following description, the gas detecting portion 3 is formed as a lump-shaped portion. Alternately, this gas detecting portion 3 may be formed as a thin film.

The gas detecting portion 3 is formed mainly of:

$(0.6 \leq x < 1; 0 \leq \delta \leq 1)$

With this sensor construction, a variation in ohmic resistance of the gas detecting portion 3 is detected.

As to the electrode construction, with the above-described construction, electric current runs also through a variable resistance portion of the gas detecting portion, such that it is possible to effectively detect a change in the ohmic resistance associated with presence of nitrogen oxide gas.

Manufacturing Methods of the Sensor

Next, methods of manufacturing the oxide compound constituting the gas detecting portion 3 will be described.

Powder materials of $Bi_2O_3$, $SrCO_3$, $CaCO_3$, $Y_2O_3$ and either Cu or CuO are mixed in a predetermined mol ratio and this mixture is calcinated in the air at 800° C. for a period of 20 hours. Thereafter, this calcinated mixture is pulverized, shaped and sintered under the following conditions.

Table 1 shows the sintering conditions provided respectively for oxide compounds (to be referred to as Samples 1 through 5 and 10) obtained by substituting values of "0", "0.2", "0.4", "0.6", "0.8 and "0.9" for the variable "x" in the above chemical formula for the gas detecting portion 3.

The electrodes 4, 5 are provided to the gas detecting portion 3, and there is also provided the heating base plate 2 under the gas detecting portion 3.

Incidentally, the compounds are not limited to the above-identified kinds, i.e. $Bi_2O_3$, $SrCO_3$, $CaCO_3$, $Y_2O_3$ and CuO. Various other kinds of compounds obtainable from a variety of combinations of the mentioned elements may be employed as well. Such other kinds of compounds include, for instance, various kinds of inorganic salts, organic salts, oxides, chlorides and hydroxides.

Characteristics of the Sensors

The sensitivity characteristics of the sensors manufactured in the above-described manner were evaluated as follows.

Figure 3:
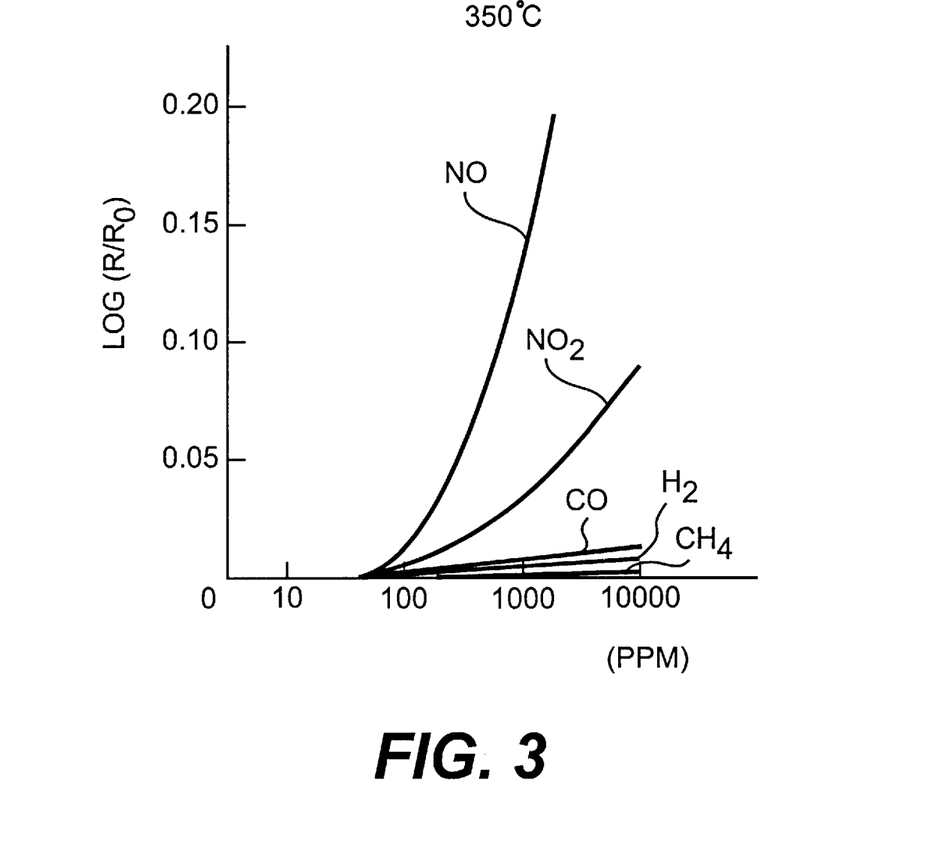
FIG. 3 is a view showing gas selectivity of the sensor.

A fixed electric potential was applied to the heating base plate 2. While the gas detecting portion was maintained at 250° C., 300° C., 350° C. and 400° C., respectively, an electric current of 10 mA was applied to the current-applying electrodes 4. Air containing a variety of components at predetermined concentrations was caused to contact the gas detecting portion, and electric potentials were measured through the potential detecting electrodes 5, to thereby obtain ohmic resistance values.

le;2qFIG. 2 shows the NO sensitivity characteristics of the Samples No. 1 through 5 identified in Table 1 at the respective temperatures (i.e., 250° C., 300° C., 350° C. and 400° C.). FIG. 3 shows the sensitivity characteristics of the Sample No. 5 at the sensor temperature of 350° C. with respect to various gases (NO, $NO_2$, CO, $H_2$, $CH_4$). In these graphs, the resistance values in the air are denoted by $R_0$ ($\Omega$) and those in the other gases are denoted by R ($\Omega$). Further, the horizontal axis in each graph represents the concentrations of the gases (unit=ppm), while the vertical axis represents the sensitivities (log (R/$R_0$)).

As described hereinbefore, for each of the Sample Nos. 1 through 5, the ratio of yttrium contained in the respective oxide compounds was increased from "0" to "0.8", in correspondence with the order of the numbering of the samples.

As a result, it was found that these sensors provided sufficient sensitivities to NO and $NO_2$. As may be seen from FIGS. 2(a), (b), (c) and (d), in terms of the content ratio of yttrium (Y), the Sample No. 5 was found to be the best. This sensor was also found to achieve the highest performance at the temperature of 350° C. Further, as shown in FIG. 3, these sensors provided satisfactory gas selectivities to the other interfering gases.

EXPERIMENTAL EXAMPLES

Experiments were conducted on a variety of materials in order to find suitable materials for the oxygen compounds forming the gas detecting portion 3. These experiments will be described next.

Table 2 shows composition formulas and crystal structures of nine types of oxide compounds evaluated. In this table, the Sample Nos. 1 through 5 and 10 are identical to those shown in Table 1.

These compositions (samples Nos. 1 through 5 and No. 10) have crystal structures comprised mainly of 2212 phase of BSCCO (see "Japan Journal of Applied Physics" M. Onoda, A. Yamamoto, E. Takayama-Muromachi and S. Takekawa vol. 27 1988 L833).

On the other hand, further Sample Nos. 6 through 9 and 11 contain, in addition to the above-identified phase, other oxide compounds comprised of calcium (Ca), strontium (Si), and copper (Cu). Here, if x=1 (i.e., no Ca is contained) in the foregoing formula, the crystal structure does not comprise the 2212 phase. The structures were determined by means of X-ray diffraction analysis.

The results of the determined analyzed compositions are shown in Table 2.2.

The X ray diffraction utilized CuK$\alpha$ rays and, for the composition analysis, the diffraction peak intensities over a diffraction angle range of 5°–65° were calculated. $\Sigma$ I[2212] is a sum of the diffraction peak intensity values based on the 2212 phase; $\Sigma$ I[2201] is a sum of the diffraction peak intensity values based on the 2201 phase; $\Sigma$ I [$Y_2O_3$] is a sum of the diffraction peak intensity values based on $Y_2O_3$; $\Sigma$ I[Bi, Ca)O] is a sum of the diffraction peak intensity values based on an oxide including one or both of Bi and Ca and excluding any other metal; $\Sigma$ I [T] is a sum of the diffraction peak intensity values of an oxide including at least one of Bi, Sr, Ca, Y and Cu, for instance, $Bi_2Sr_2$ $(Ca_{0.2}Y_{0.8})$ $Cu_2O_{8\pm\delta}$, $Y_2O_3$ (a compound including an element except Bi, Sr, Ca, Y, and Cu; for instance, $SrTiO_3$ is excluded.)

However, the gas detecting portion may include a stable oxide including any element except Bi, Sr, Ca, Y and Cu, e.g., $SrTiO_3$, $SiO_2$ or the like). These compounds do not affect the $NO_x$ detecting function, but just enhance the mechanical or chemical strength of the material forming the gas detecting portion.

Figure 4:
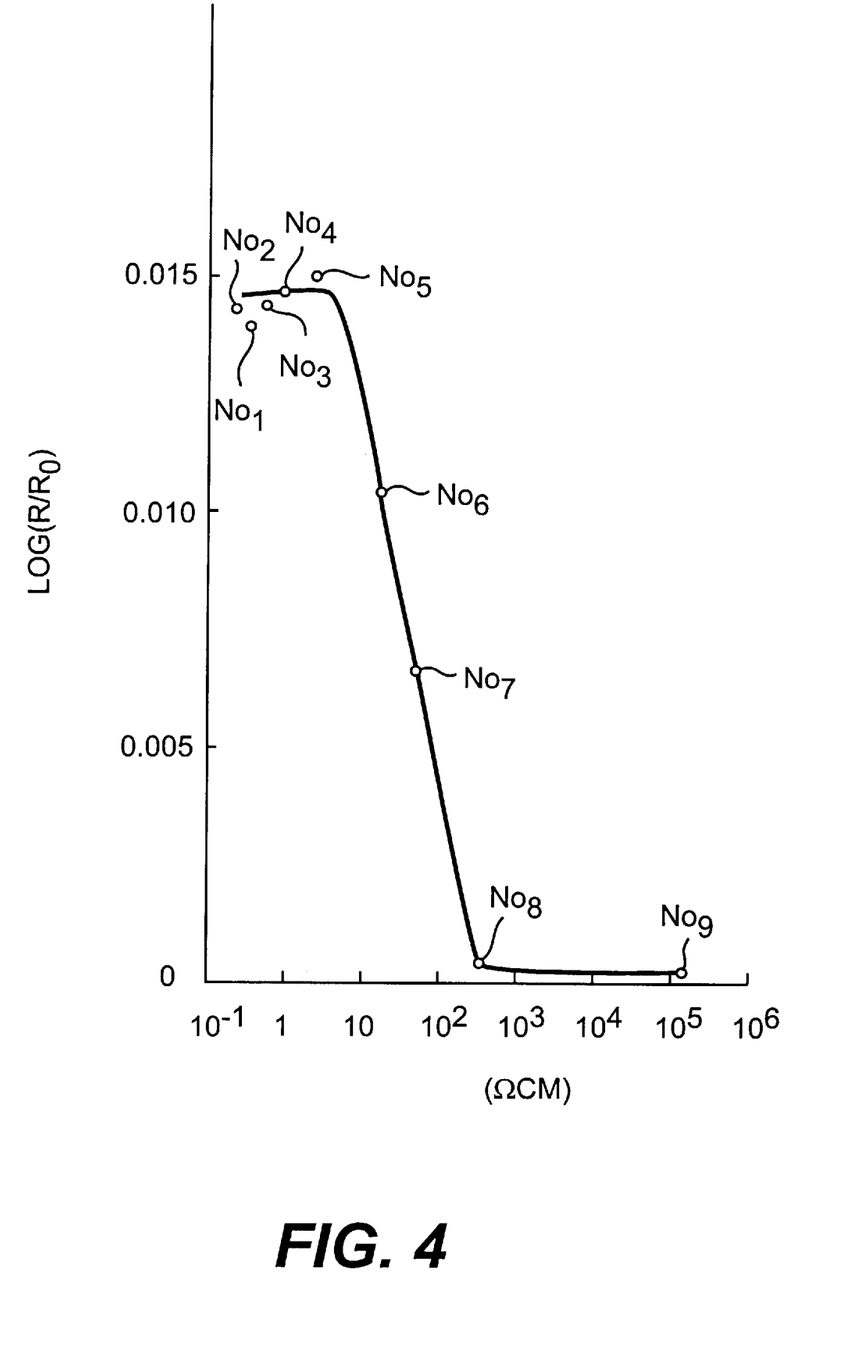
FIG. 4 is a view illustrating the relationship between sensitivity and resistivity of materials having different crystal structures.
Figure 5A:
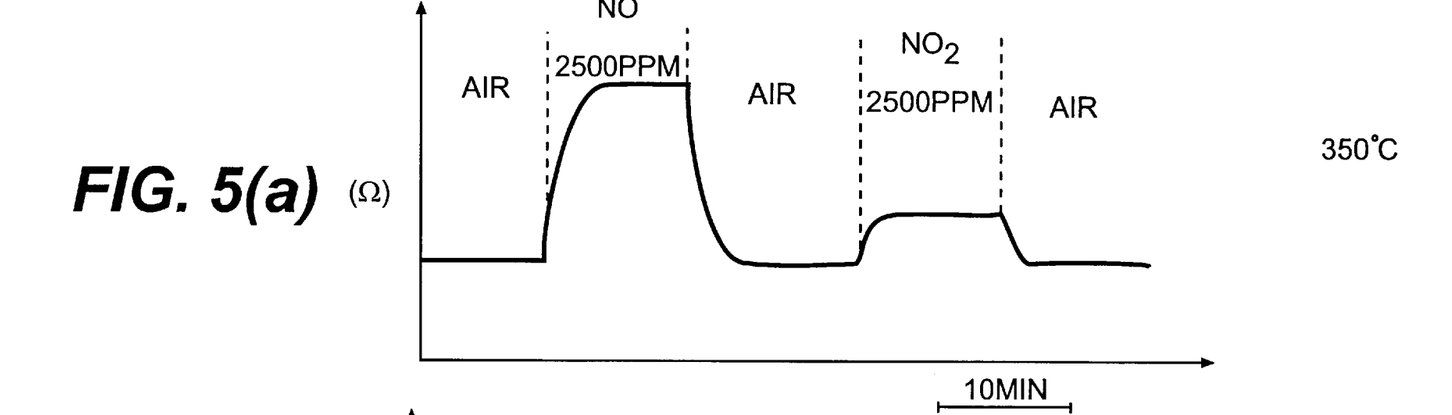
FIGS. 5(a), (b), (c) and (d) are views illustrating reversible characteristics of the sensor having materials of different crystal structures.
Figure 5B:
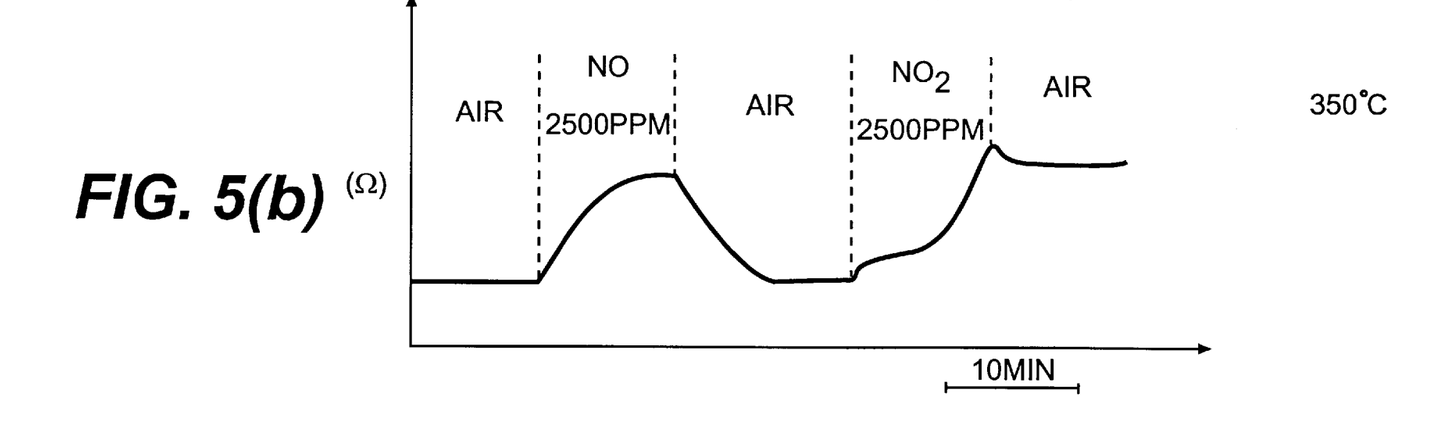
Figure 5C:
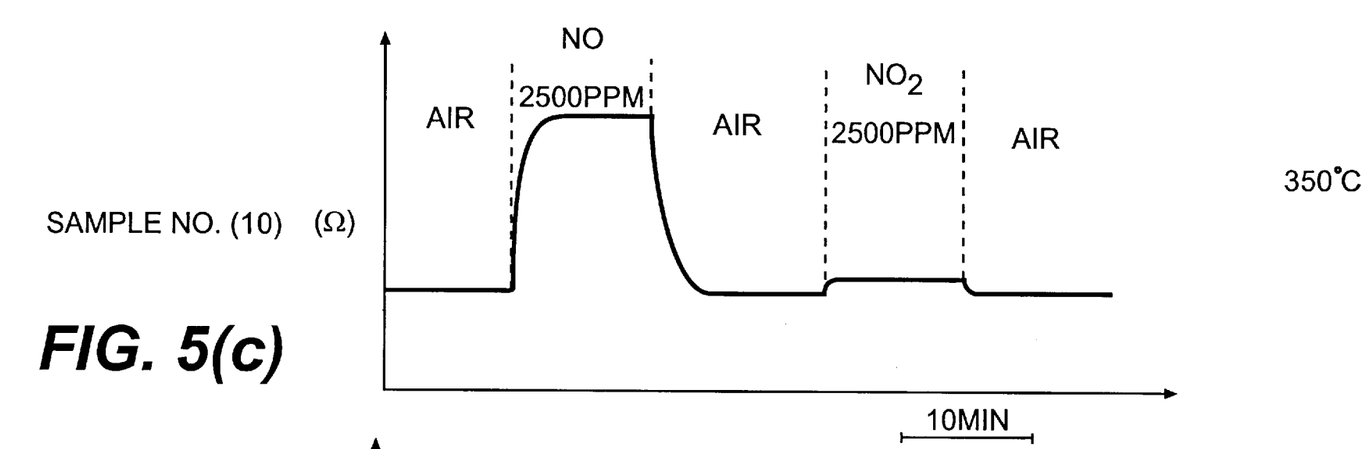
Figure 5D:
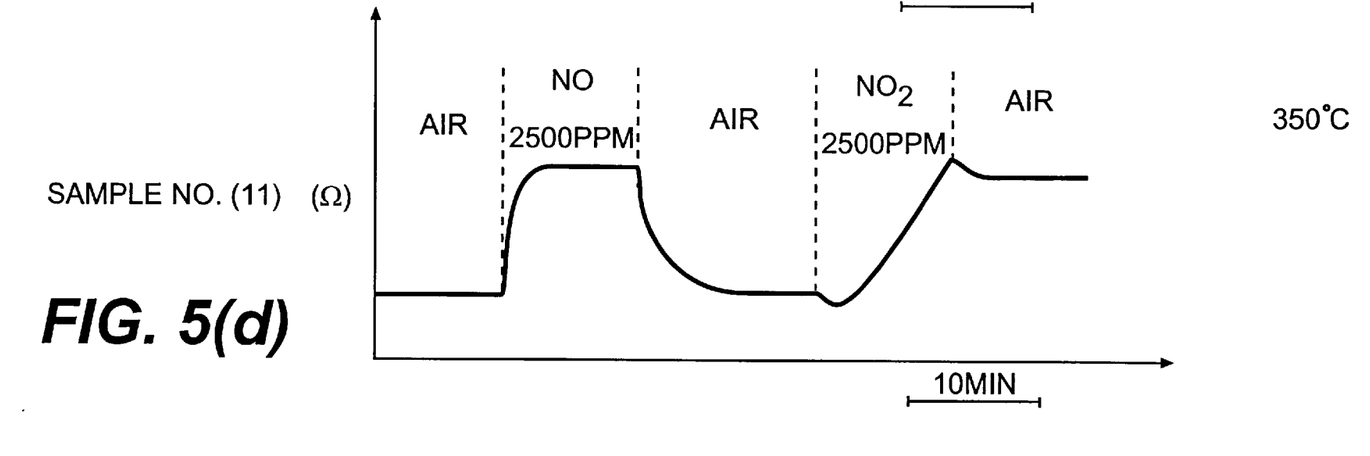

FIG. 4 shows the relationships between the resistivities and the sensitivities of the above-described Sample Nos. 1 through 9. Further, FIG. 5 shows sensor reversibility characteristics of the Sample sensors Nos. 5 and 8 with respect to NO gas and $NO_2$ gas.

FIG. 5 (a) shows the results of the Sample No. 5 and FIG. 5(b) shows the results of the Sample No. 8. In each of these drawings, the horizontal axis represent the time lapse while the vertical axes represent the change in the ohmic resistance values (Ω). In the earlier stages of the experiments, the sensors were caused to contact NO gas. Then, after contact with air, the sensors were caused to contact $NO_2$ gas.

From FIG. 4, it may be understood that the sensitivities to the nitrogen oxides vary depending on the sample structures. As shown in FIG. 4, higher sensitivity was obtained from the Sample Nos. 1 through 5 having crystal structures comprised mainly of 2212 phase. Concerning the resistivities, those having resistivities less than 50 Ω cm achieved satisfactory sensitivities.

Referring now to FIG. 5, the Sample No. 5 showed reversible sensitivity to both NO gas and $NO_2$ gas. On the other hand, the Sample No. 8 did not show reversible sensitivity to $NO_2$ gas.

To consider the possible reason for the above fact, the Sample No. 5 is comprised mainly of the single phase consisting solely of 2212 phase, while the Sample No. 8 includes the phases other than 2212 phase, such as the oxide compound of Ca and Cu. Then, in this Sample No. 8, the oxide compound of Ca and Cu irreversibly absorbs $NO_2$, thereby preventing the ohmic resistance of this Sample No. 8 from restoring to its initial value after $NO_2$ is eliminated. Further similar experiments were conducted on the Sample Nos. 1 through 4, 6, 7. In these experiments too, the above-described relationship between the crystal structure and the ohmic resistance value applied.

The above description to the effect that Sample No. 5 comprised mainly of the single phase consisting solely of 2212 phase means that the diffraction peak values having a sum $\Sigma$ I [2212] may be expressed by one of the following:

(a) $\Sigma$ I[2212]/$\Sigma$ I[T]>88.1%
(b) {$\Sigma$ I[2212]+$\Sigma$ I[2201]}/$\Sigma$ I[T]>94.8%
(c) {$\Sigma$ I[2212]+$\Sigma$ I[$Y_2O_3$]} $\Sigma$ I[T]>88.1%
(d) {$\Sigma$ I[2212]+$\Sigma$ I[(Bi, Ca) O]}/$\Sigma$ I[T]>88.8%

Figure 6:
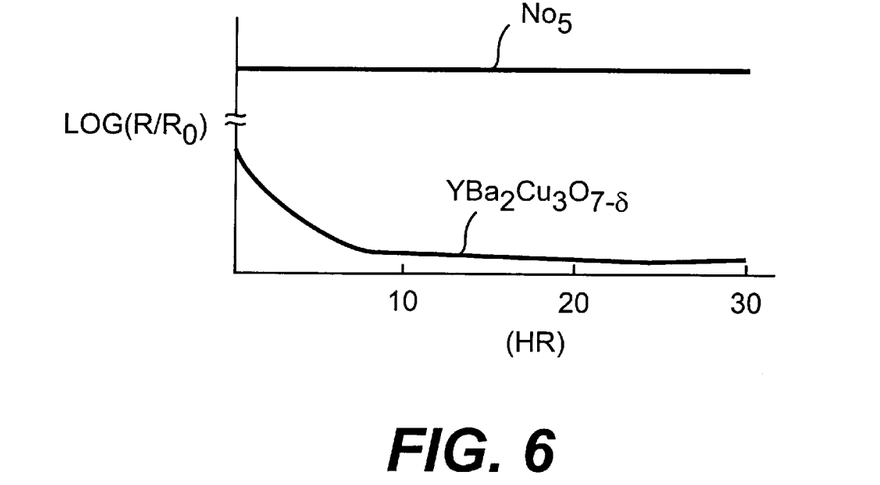
FIG. 6 is a view showing secular changes in the sensitivity of the oxide compound.

As to the durability of the sensor, as shown in FIG. 6, the conventional type expressed by the formula:

$YBa_2 Cu_3O_{7-\delta}$ loses its sensitivity substantially entirely after a period of 10 hours under humidified conditions. In contrast, in the case of the sensors according to the composition of the present invention, there occurs no secular change from the initial value thereof. Accordingly, it may be considered that the sensor according to the present invention provides sufficient durability.

Next, some other experimental examples will be described.

Figure 7:
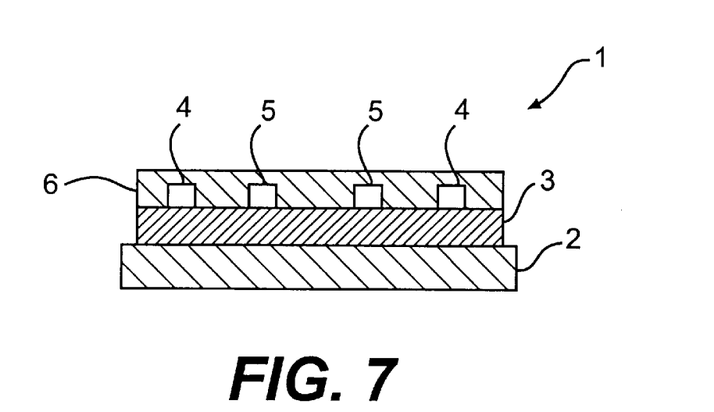
FIG. 7 is a view showing a construction of a sensor according to a further embodiment of the invention, the sensor having an oxidation catalyst layer.

(1) A construction having an oxidation catalyst layer 6:

In this case, the sensor 1 having the above-described construction is provided further with an oxidation catalyst layer 6 including an element belonging in the platinum group, such as platinum (Pt), palladium (Pd) or the like, for eliminating, through an oxidation reaction, the above-identified interfering components (CO, $H_2$, $CH_4$ and also $C_2H_5OH$, $CH_3OH$ or the like). This sensor too is effective for the detection of nitrogen oxides. The construction of this sensor is shown in FIG. 7.

As one method for forming this oxidation catalyst layer 6, a substance comprised of activated alumina dispersedly mixed with about 1% of the platinum group element is screen-printed, in the thickness of 500 μm approximately, on the film of the gas detecting portion 3 and then sintered.

In addition to the above-described construction, further constructions may be obtained by:

(a) adding and mixing about 0 to 2% of a platinum group element such as Pt, Pd or the like to the oxide compound; or (b) causing a platinum group element such as Pt, Pd or the like to be carried on the surface of the oxide compound.

Electrode Construction

In the foregoing embodiment, the pair of current-applying electrodes 4 and the pair of potential-detecting electrodes 5 are provided for detecting change in the ohmic resistance value. Instead, it is conceivable to apply a fixed potential between a pair of potential-applying electrodes and to detect the electric current between a pair of current-detecting electrodes.

As a further electrode construction, it is possible to employ conventional two-terminal electrodes (each acting as both a current electrode and a potential electrode). In this case, however, at a part of the gas detecting portion, there occurs a partial resistance change due to absorption of nitrogen oxide, so that the electric current predominantly flows only through a lower resistance part. Accordingly, the change in the resistance value at the gas detecting portion detectable through the electrodes may be very small. In this sense, the structures described in the above embodiments are more desirable.

However, any other type of electrode construction will be possible as long as the construction allows effective detection of change in the resistance value taking place at the gas detecting portion.

Heating Means

In order to improve the responsiveness and restorability of the ohmic resistance value of the nitrogen oxide sensor in response to a change in the nitrogen oxide gas concentration, it is preferred that the sensor be heated higher than 250° C. as described in the foregoing embodiment. For this purpose, any appropriate heating means such as the ceramic heating plate employed in the described embodiment should be provided. As this heating means, it is also conceivable to surround the entire sensor with a heater coil or to surround only a portion of the sensor with such a heater coil with the remaining portion thereof being heated by the ceramic heater plate.

The provision of the heating means may sufficiently accelerate the absorption and discharge of the nitrogen oxide, to thereby improve the responsiveness and restorability of the ohmic resistance value of the nitrogen oxide sensor in response to a change in the nitrogen oxide gas concentration.

However, such heating means will not be needed for the detection as long as a sufficient amount of change in the resistance value may be obtained. Further, a self-heating type construction is conceivable in which the base plate per se is supplied with electric current to be heated thereby.

Sensor Configuration

The configuration of the gas detecting portion 3 is not limited to the lump-like configuration described hereinbefore. Any other type of configuration is also possible such as a thin-film-like configuration. With such a configuration, the gas detecting portion may also provide the detecting function.

Methods of Forming a Thin Film

As the method for forming a thin film of the gas detecting portion, in addition to the laser abrasion method, other methods are also possible such as the physical vapor deposition methods that include the vacuum vapor deposition method and the sputtering method, as well as the chemical vapor deposition methods which include MO-CVD (Metal Organic Chemical Vapor Deposition) method and the chloride CVD method.

Figure 8:
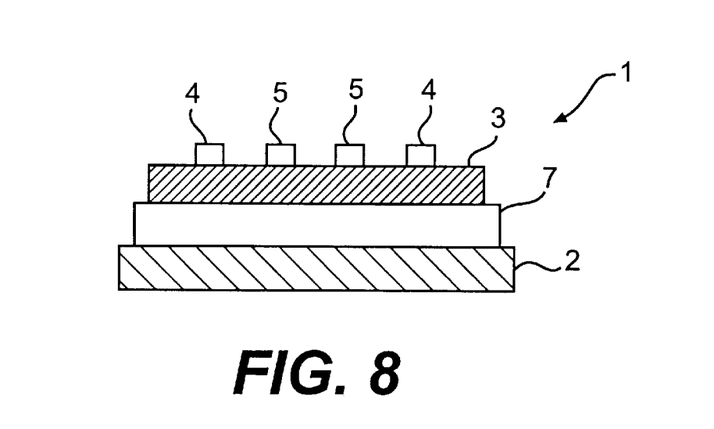
FIG. 8 is a view showing a construction of a sensor according to a still further embodiment of the invention.

As an even further embodiment of the present invention, the sensor may be constructed as shown in FIG. 8.

In the case of a nitrogen oxide detecting sensor 1 according to this embodiment, a gas detecting portion 3 in the form of a thin film is formed on one surface of a deposition substrate 7. On the opposite surface of the deposition substrate 7, there is disposed a heating base plate 2 incorporating a heater. Then, for this gas detecting portion 3, there are provided a pair of current-applying electrodes 4 and a corresponding pair of potential-detecting electrodes 5, in the same manner as the foregoing embodiment. In this embodiment, the gas detecting portion 3 may also be formed as a thin film. With this sensor construction, nitrogen oxides may be effectively detected.

In the case of the deposition substrate 7 shown in FIG. 8, a poly-crystalline ceramic plate is generally used based on economic considerations. However, when higher sensor performance (higher sensitivity, a higher stability and so on) is desired, a single-crystalline ceramic plate may be used for forming the gas detecting portion 3 in the form of a thin film comprised of the oxide compound predetermined according to the present invention. As such, single-crystalline ceramic plates, single-crystalline alumina (sapphire, $Al_2O_3$), single-crystalline magnesia (MgO), single-crystalline strontium titanate ($SrTiO_3$) or the like may be employed. In such cases, because of the absence of a crystal grain phase, the thin-film gas detecting portion formed on the surface of the deposition substrate will achieve a higher formation precision (especially, the precision of its thickness) and the thus-formed thin film will obtain a more complete and defectless crystal structure. Consequently, a sensor of higher performance may be obtained.

The invention may be embodied in other specific forms without departing from the spirit or essential characteristics thereof. The present embodiments are therefore to be considered in all respects as illustrative and not restrictive, the scope of the invention being indicated by the appended claims rather than the foregoing description and all changes which become within the meaning and range of equivalency of the claims are therefore intended to be embraced therein.

TABLE 1

| sample No. | X | composition | sintering conditions |
|---|---|---|---|
| 1 | 0 | $Bi_2Sr_2CaCu_2O_{8+\delta}$ | 840° C. 30 hr in air |
| 2 | 0.2 | $Bi_2Sr_2(Ca_{0.8}Y_{0.2})Cu_2O_{8\pm\delta}$ | 870° C. 30 hr in air |
| 3 | 0.4 | $Bi_2Sr_2(Ca_{0.6}Y_{0.4})Cu_2O_{8\pm\delta}$ | 910° C. 30 hr in air |
| 4 | 0.6 | $Bi_2Sr_2(Ca_{0.4}Y_{0.6})Cu_2O_{8\pm\delta}$ | 930° C. 30 hr in air |
| 5 | 0.8 | $Bi_2Sr_2(Ca_{0.2}Y_{0.8})Cu_2O_{8\pm\delta}$ | 930° C. 30 hr in air |
| 10 | 0.9 | $Bi_2Sr_2(Ca_{0.1}Y_{0.9})Cu_2O_{8\pm\delta}$ | 930° C. 30 hr in air |

TABLE 2

| sample No. | composition | structure |
|---|---|---|
| 1 | $Bi_2Sr_2CaCu_2O_{8\pm\delta}$ | mainly 2212 phase of BSCCO |
| 2 | $Bi_2Sr_2(Ca_{0.8}Y_{0.2})Cu_2O_{8\pm\delta}$ | mainly 2212 phase of BSCCO |
| 3 | $Bi_2Sr_2(Ca_{0.6}Y_{0.4})Cu_2O_{8\pm\delta}$ | mainly 2212 phase of BSCCO |
| 4 | $Bi_2Sr_2(Ca_{0.4}Y_{0.6})Cu_2O_{8\pm\delta}$ | mainly 2212 phase of BSCCO |
| 5 | $Bi_2Sr_2(Ca_{0.2}Y_{0.8})Cu_2O_{8\pm\delta}$ | mainly 2212 phase of BSCCO |
| 6 | $Bi_2Sr_2CaCu_2O_{8\pm\delta}$ | 2212 phase, 2201 phase and complex oxide of Ca, Sr, Cu |
| 7 | $Bi_2Sr_2CaCu_2O_{8\pm\delta}$ | 2212 phase, and complex oxide of Ca, Sr, Cu |
| 8 | $Bi_2Sr_2CaCu_2O_{8\pm\delta}$ | 2212 phase, and complex oxide of Ca, Sr, Cu and Ca, Cu |
| 9 | $Bi_2Sr_2CaCu_2O_{8\pm\delta}$ | 2212 phase, 2201 phase, and complex oxide of Ca, Sr, Cu |
| 10 | $Bi_2Sr_2(Ca_{0.1}Y_{0.9})Cu_2O_{8\pm\delta}$ | mainly 2212 phase of BSCCO |
| 11 | $Bi_2Sr_2(Ca_{0.1}Y_{0.9})Cu_2O_{8\pm\delta}$ | 2212 phase, and complex oxide of Ca, Sr, Cu |

TABLE 2.2

| sample No. | composition | $\Sigma I[2212] / \Sigma I[T]$ | $\Sigma I[2212] + \Sigma I[2201] / \Sigma I[T]$ | $\Sigma I[2212] + \Sigma I[Y_2O_3] / \Sigma I[T]$ | $\Sigma I[2212] + \Sigma I[(Bi,Ca)O] / \Sigma I[T]$ |
|---|---|---|---|---|---|
| 1 (1) | $Bi_2Sr_2CaCu_2O_{8\pm\delta}$ | 87.2% | 87.2% | 87.2% | 98.1% |
| 1 (2) | $Bi_2Sr_2CaCu_2O_{8\pm\delta}$ | 98.8% | 98.8% | 98.8% | 98.8% |
| 1 (3) | $Bi_2Sr_2CaCu_2O_{8\pm\delta}$ | 97.0% | 97.0% | 97.0% | 97.0% |
| 4 | $Bi_2Sr_2(Ca_{0.4}Y_{0.6})Cu_2O_{8\pm\delta}$ | 97.9% | 97.9% | 100.0% | 97.9% |
| 5 | $Bi_2Sr_2(Ca_{0.2}Y_{0.8})Cu_2O_{8\pm\delta}$ | 96.8% | 96.8% | 100.0% | 96.8% |
| 6 | $Bi_2Sr_2CaCu_2O_{8\pm\delta}$ | 88.1% | 92.2% | 88.1% | 88.8% |
| 9 | $Bi_2Sr_2CaCu_2O_{8\pm\delta}$ | 47.9% | 94.8% | 47.9% | 47.9% |
| 10 | $Bi_2Sr_2(Ca_{0.1}Y_{0.9})Cu_2O_{8\pm\delta}$ | 97.1% | 97.1% | 97.1% | 97.1% |
| 11 | $Bi_2Sr_2(Ca_{0.1}Y_{0.9})Cu_2O_{8\pm\delta}$ | 78.2% | 78.2% | 80.1% | 78.2% |

We claim:

1. A nitrogen oxide detecting sensor, comprising:

means for detecting gas including a gas detecting portion composed mainly of an oxide compound having electric conductivity or semiconductivity, said oxide compound including a crystal structure of 2212 phase and expressed generally as:

$Bi_2Sr_2(Ca_{1-x}Y_x)Cu_2O_{8+y}$ where $0.6 \leq x < 1$, $0 \leq y \leq 1$, wherein, said gas detecting portion includes a structural composition having, when analyzed by x-ray diffraction using CuK α rays, diffraction peak values thereof with a diffraction angle in the range between 5° and 65°, a sum of diffraction peak intensity values Σ[T] being expressed by one of the following:
(a) Σ I[2212]/ Σ I[T]>88.1%
(b) {ΣI[2212]+ΣI[2201]}/ΣI[T]>94.8%
(c) {ΣI[2212]+ΣI[Y₂O₃]}/Σ[T]>88.1%
(d) {ΣI[2212]+ΣI[(Bi, Ca)O]}/ΣI[T]>88.8% where ΣI[2212] is a sum of diffraction peak intensity values based on a 2212 phase, ΣI[2201] is a sum of diffraction peak intensity values based on a 2201 phase, ΣI[Y₂O₃] is a sum of diffraction peak intensity values based on Y₂O₃, ΣI[(Bi, Ca)O] is a sum of diffraction peak intensity values based on an oxide including one or both of Bi and Ca excluding any other metal, and ΣI[T] is a sum of diffraction peak intensity values based on an oxide including at least one of Bi, Sr, Ca, Y and Cu;

electrodes electrically connected to said gas detecting portion; and heating means for maintaining the gas detection portion at an operating temperature above 250° C., wherein the gas detecting portion includes means for providing an electric detection value obtained though the electrodes in the absence of N0₂, which value remains unchanged before and after the NO₂, detection.

2. A nitrogen oxide detecting sensor as defined in claim 1, wherein said gas detecting portion further includes at least one kind of a metal oxide non-reactive to nitrogen oxide.

3. A nitrogen oxide detecting sensor as defined in claim 2, wherein an oxidation catalyst layer containing a platinum group element including Pt, Pd is provided at least on an outer side of said gas detecting portion.

4. A nitrogen oxide detecting sensor as defined in claim 2, wherein a platinum group element including Pt, Pd is supported at least on an outer side of said gas detecting portion.

5. A nitrogen oxide detecting sensor as defined in claim 2, wherein said gas detecting portion comprises a thin film made on a deposition substrate.

6. A nitrogen oxide detecting sensor as defined in claim 5, wherein said deposition substrate comprises a ceramic plate.

7. A nitrogen oxide detecting sensor as defined in claim 5, wherein said deposition substrate is mounted on a heating base plate.

8. A nitrogen oxide detecting sensor as defined in claim 7, wherein said heating base plate is composed of a ceramic material.

9. A nitrogen oxide detecting sensor as defined in claim 2, wherein said gas detecting portion is mounted on a heating base plate.

10. A nitrogen oxide detecting sensor as defined in claim 9, wherein said heating base plate is composed of a ceramic material.

11. A nitrogen oxide detecting sensor as defined in claim 1, wherein an oxidation catalyst layer containing a platinum group element including Pt, Pd is provided at least on an outer side of said gas detecting portion.

12. A nitrogen oxide detecting sensor as defined in claim 1, wherein a platinum group element including Pt, Pd is supported at least on an outer side of said gas detecting portion.

13. A nitrogen oxide detecting sensor as defined in claim 1, wherein said gas detecting portion comprises a thin film made on a deposition substrate.

14. A nitrogen oxide detecting sensor as defined in claim 13, wherein said deposition substrate comprises a ceramic plate.

15. A nitrogen oxide detecting sensor as defined in Claim 13, wherein said deposition substrate is mounted on a heating base plate.

16. A nitrogen oxide detecting sensor as defined in claim 15, wherein said heating base plate is composed of a ceramic material.

17. A nitrogen oxide detecting sensor as defined in claim 1, wherein said gas detecting portion is mounted on a heating base plate.

18. A nitrogen oxide detecting sensor as defined in claim 17, wherein said heating base plate is composed of a ceramic material.

19. A nitrogen oxide detecting sensor having sensitivity to the nitrogen oxides, comprising:

means for detecting the nitrogen oxides including a gas detecting portion composed mainly of material having electric conductivity or semiconductivity and expressed generally by a general formula: $Bi_2Sr_2(Ca_{1-x}Y_x)Cu_2O_{8+y}$ wherein, the main material of said gas detecting portion comprises an oxide compound which satisfies $0.6 \leq x < 1$, $0 \leq y \leq 1$ in said general formula, and has a resistivity of 50 Ω cm or lower at said operating temperature;

electrodes electrically connected to said gas detecting portion; and heating means for maintaining the gas detection portion at an operating temperature above 250° C., said gas detecting portion having means for providing an electric detection value obtained though the electrodes in the absence of NO₂, which value remains unchanged before and after the NO₂ detection.

* * * * *